US 9,517,090 B2

(12) United States Patent
Harper et al.

(10) Patent No.: US 9,517,090 B2
(45) Date of Patent: *Dec. 13, 2016

(54) POLYAXIAL CROSS CONNECTOR

(71) Applicant: GLOBUS MEDICAL, INC., Audubon, PA (US)

(72) Inventors: Michael Harper, Pottstown, PA (US); Devjeet Mishra, Philadelphia, PA (US); Derek Martzall, Sinking Springs, PA (US)

(73) Assignee: Globus Medical, Inc., Audubon, PA (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/725,406

(22) Filed: May 29, 2015

(65) Prior Publication Data

US 2015/0257790 A1 Sep. 17, 2015

Related U.S. Application Data

(63) Continuation of application No. 13/669,527, filed on Nov. 6, 2012, now Pat. No. 9,072,547.

(51) Int. Cl.
*A61B 17/70* (2006.01)
*A61B 17/80* (2006.01)

(52) U.S. Cl.
CPC ......... *A61B 17/705* (2013.01); *A61B 17/7052* (2013.01); *A61B 17/7055* (2013.01); *A61B 17/809* (2013.01)

(58) Field of Classification Search
CPC ............ A61B 17/6458; A61B 17/6466; A61B 17/6491; A61B 17/6416; A61B 17/6425; A61B 17/6441; A61B 17/7049; A61B 17/705; A61B 17/7052

See application file for complete search history.

(56) References Cited

U.S. PATENT DOCUMENTS

| 5,098,432 | A | 3/1992 | Wagenknecht |
| 5,676,665 | A | 10/1997 | Bryan |
| 6,554,831 | B1 | 4/2003 | Rivard et al. |
| 6,554,832 | B2 | 4/2003 | Shluzas |
| 7,122,036 | B2 | 10/2006 | Vanacker |
| 7,569,070 | B2 | 8/2009 | Suzuki et al. |
| 7,744,632 | B2 * | 6/2010 | Usher ................ A61B 17/7052 606/250 |

(Continued)

*Primary Examiner* — Lynnsy Summitt

(57) ABSTRACT

A device and method for coupling first and second elongate spinal fixation elements. The device includes first and second connector members, for receiving first and second elongate spinal fixation elements respectively. One or both connector members may include an engagement portion configured and dimensioned to provisionally receive an elongate fixation element with an interference fit. First and second connector members are coupled to a translation member, the translation member operatively associated with at least one connector member to provide for polyaxial movement. At least one locking member is provided to secure a received elongate spinal fixation element in the engagement portion and lock polyaxial movement of the at least one connector member. The translation member may have first and second portions which move relative to each other with translation movement, and a third locking member to lock the translation movement.

20 Claims, 9 Drawing Sheets

(56) References Cited

U.S. PATENT DOCUMENTS

| | | | |
|---|---|---|---|
| 7,833,251 B1 | 11/2010 | Ahlgren et al. | |
| 7,922,747 B2 | 4/2011 | Kirschman | |
| 8,075,594 B2 | 12/2011 | Purcell | |
| 8,080,037 B2 | 12/2011 | Butler et al. | |
| 8,167,908 B2 | 5/2012 | Ely et al. | |
| 8,241,334 B2 | 8/2012 | Butler et al. | |
| 8,292,924 B2 | 10/2012 | Neary et al. | |
| 8,480,712 B1 | 7/2013 | Samuel et al. | |
| 8,568,456 B2 | 10/2013 | Black | |
| 8,617,213 B2 | 12/2013 | Moore et al. | |
| 8,672,978 B2 | 3/2014 | Dant et al. | |
| 8,771,319 B2 | 7/2014 | Prajapati | |
| 2003/0028192 A1 | 2/2003 | Schar et al. | |
| 2003/0114853 A1 | 6/2003 | Burgess et al. | |
| 2005/0090821 A1 | 4/2005 | Berrevoets et al. | |
| 2006/0206114 A1 | 9/2006 | Ensign et al. | |
| 2006/0229616 A1 | 10/2006 | Albert et al. | |
| 2007/0049932 A1 | 3/2007 | Richelsoph et al. | |
| 2007/0225713 A1 | 9/2007 | Altarac et al. | |
| 2008/0103507 A1 | 5/2008 | Purcell | |
| 2008/0172093 A1 | 7/2008 | Nilsson | |
| 2008/0306538 A1* | 12/2008 | Moore | A61B 17/7052 606/250 |
| 2011/0137345 A1 | 6/2011 | Stoll et al. | |
| 2012/0035659 A1* | 2/2012 | Barrus | A61B 17/7049 606/251 |
| 2012/0226316 A1 | 9/2012 | Dant et al. | |
| 2013/0006307 A1 | 1/2013 | Robinson et al. | |
| 2013/0030468 A1 | 1/2013 | Le Couedic et al. | |
| 2013/0165976 A1 | 6/2013 | Gunn | |

\* cited by examiner

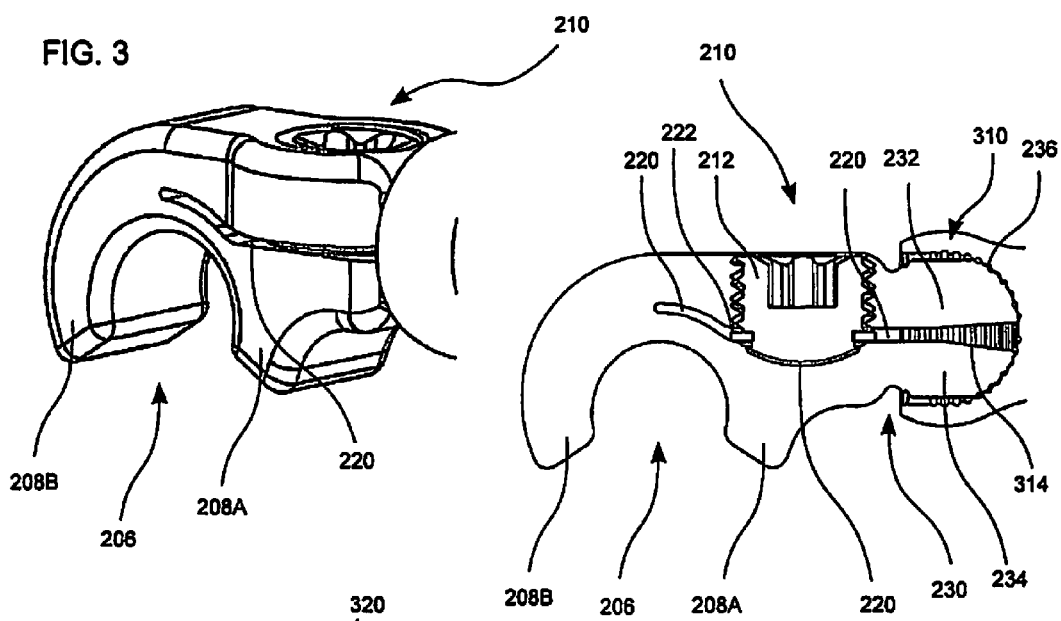
FIG. 3
FIG. 4
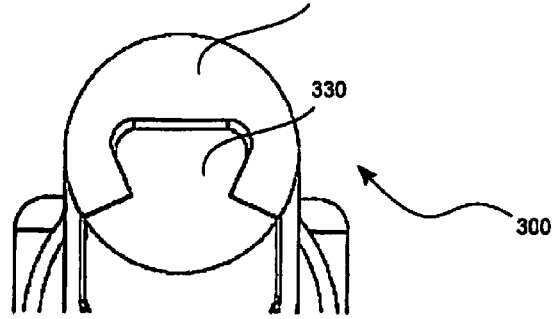
FIG. 5
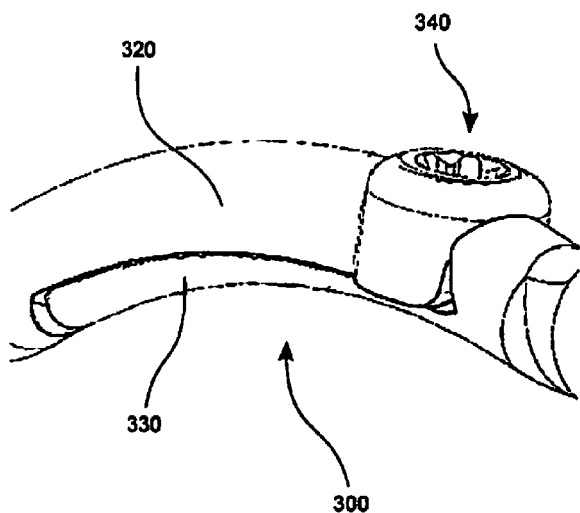
FIG. 6

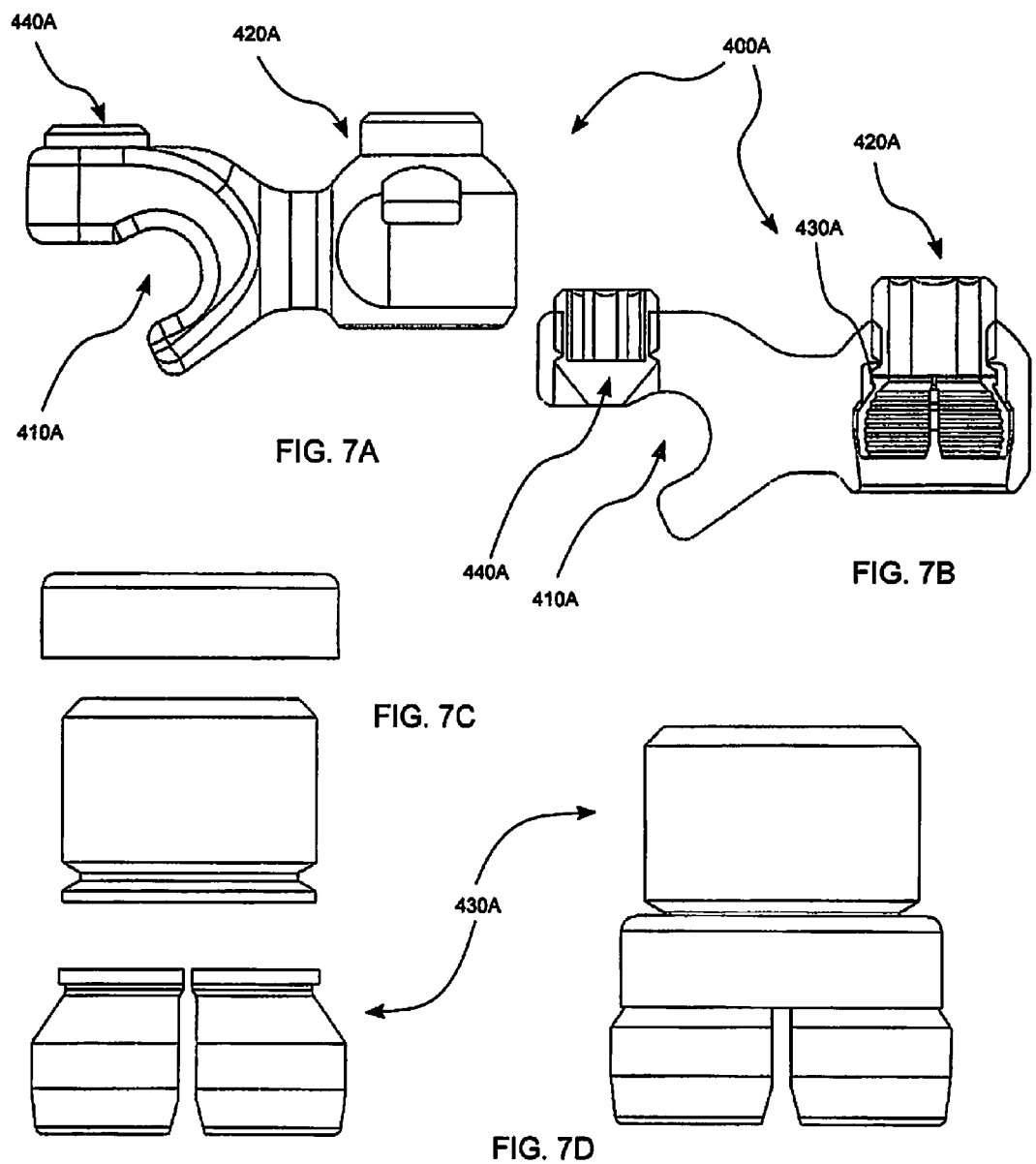

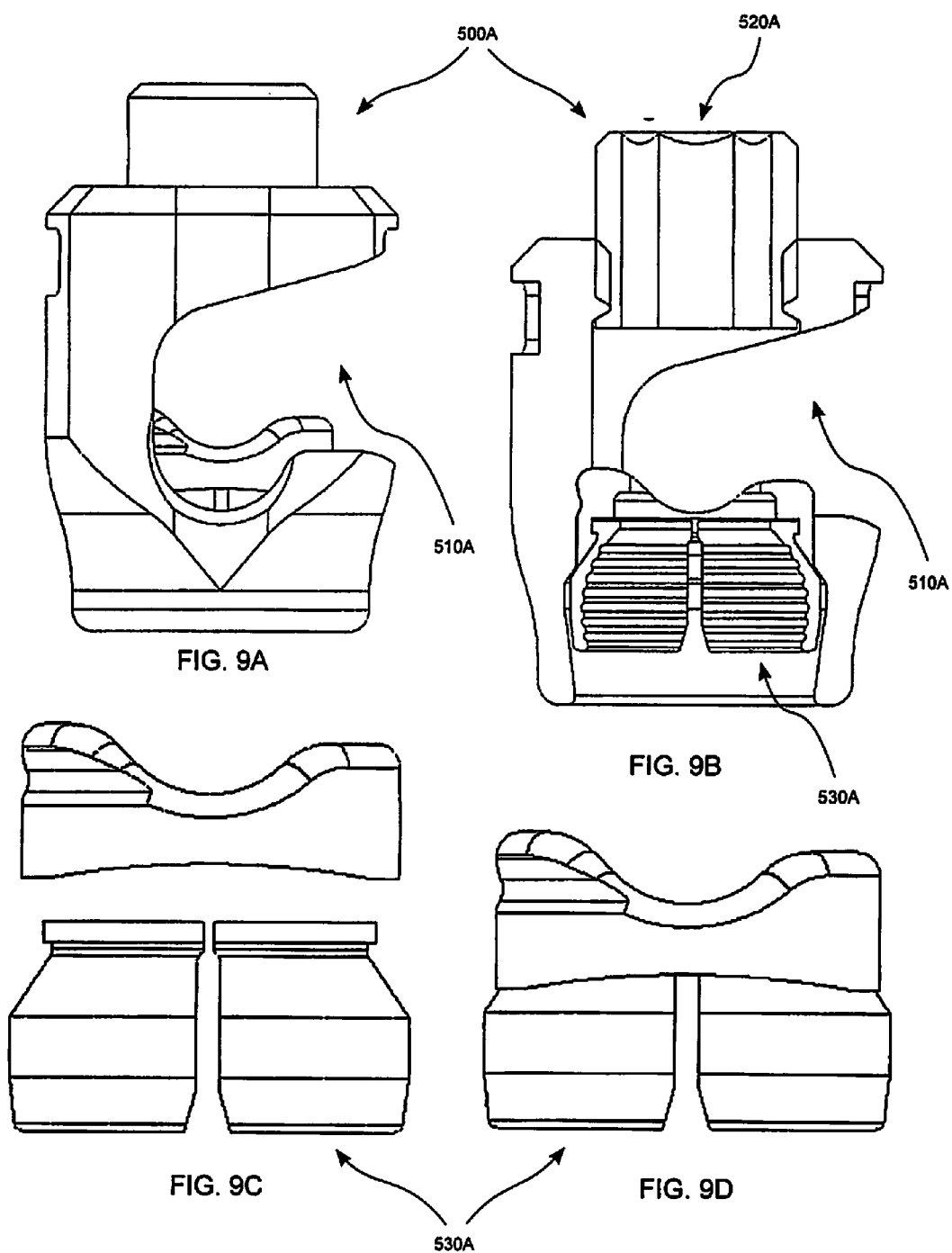

FIG. 11A
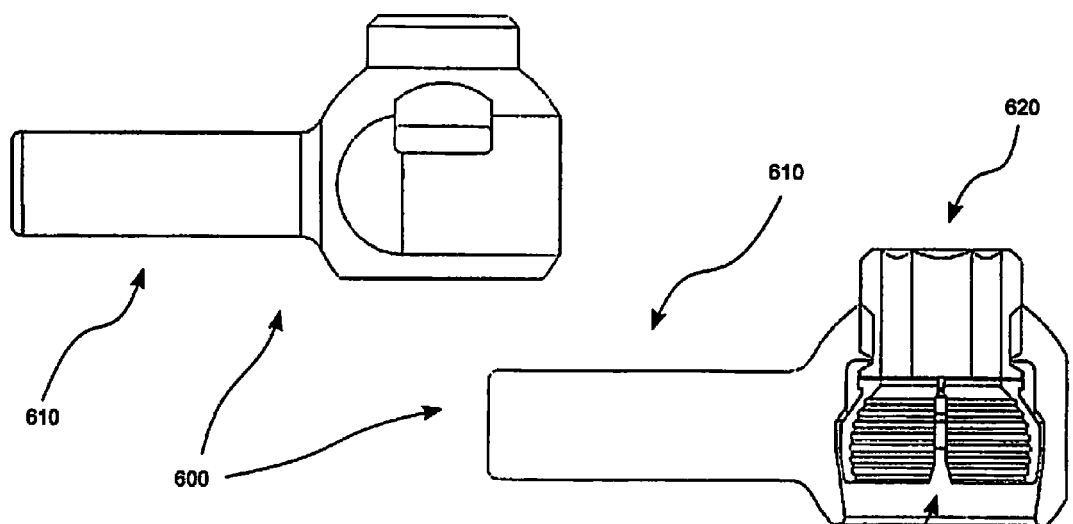
FIG. 11B
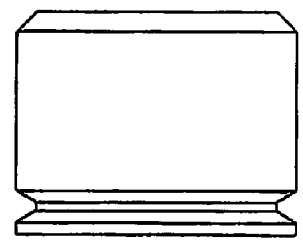
FIG. 11C
FIG. 11D

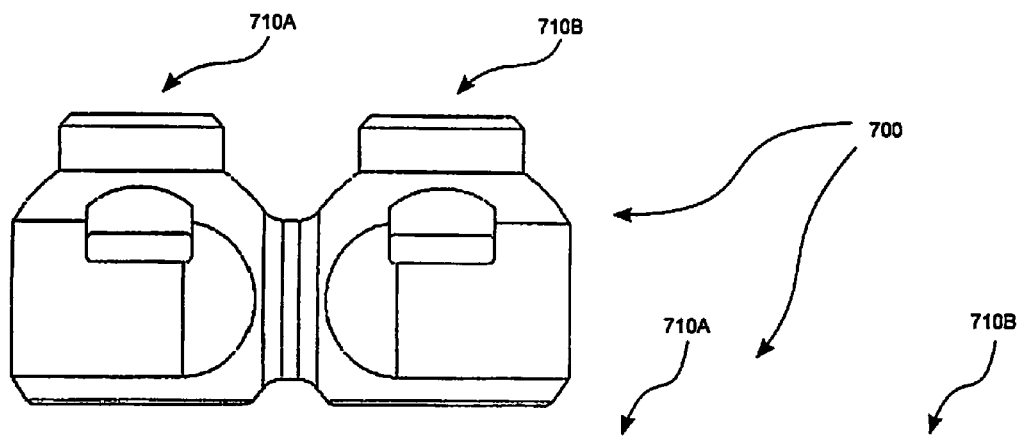
FIG. 12A
FIG. 12B
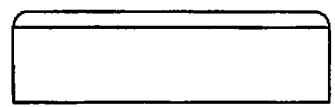
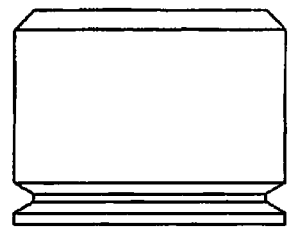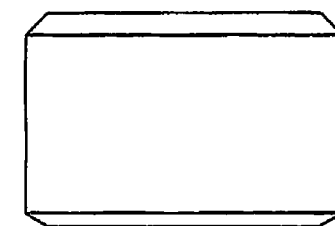
FIG. 12C          FIG. 12D

POLYAXIAL CROSS CONNECTOR

CROSS REFERENCE TO RELATED APPLICATION

This application is a continuation of U.S. application Ser. No. 13/669,527, filed on Nov. 6, 2012, which is hereby incorporated by reference in its entirety for all purposes.

FIELD OF THE INVENTION

The invention relates to connectors for fixation elements, including interconnecting at least two spinal fixation rods.

BACKGROUND OF THE INVENTION

Bones and bony structures are susceptible to a variety of weaknesses that can affect their ability to provide support and structure. Weaknesses and deformities in bony structures have numerous potential causes, including degenerative diseases, tumors, fractures, and dislocations. Advances in medicine and engineering have provided health care practitioners with a number of devices and techniques for alleviating or curing those weaknesses.

With respect to the spinal column, additional support may be necessary to address such weaknesses and deformities. Surgical techniques for stabilizing the spinal column, such as spinal fusion, have been developed to eliminate pain and other detrimental effects associated with spinal column defects. The placement of one or more screws, rods, plates, or cages may be required in association with some spinal stabilization techniques.

The strength and stability of a dual rod, plate, or other elongate member assembly can be increased by coupling the two rods with a cross connector which extends substantially horizontal to the longitudinal axes of the rods across the spine. Due to a wide variety of factors, the two rods are rarely geometrically aligned in clinical situations. A cross connector with at least some adjustability can be provided to accommodate for variations from geometrical alignment.

SUMMARY OF THE INVENTION

The invention relates to a device for coupling first and second elongate spinal fixation elements. The device includes a first connector member having proximal and distal portions, the distal portion including an engagement portion configured and dimensioned to provisionally receive the first elongate spinal fixation element with an interference fit; a translation member having proximal and distal portions the proximal portion of the first connector member operatively associated with the proximal portion of the translation member to provide polyaxial movement of the first connector member relative to the translation member; a second connector member having proximal and distal portions, the distal portion configured and dimensioned to receive the second elongate spinal fixation element and the proximal portion coupled to the translation member; and a first locking member to secure the first elongate spinal fixation element in the engagement portion of the first connector member and to lock the polyaxial movement, fixing the first connector member relative to the first translation member.

In additional embodiments in accordance with the disclosure, the proximal portion of the first connector member includes a sphere and the distal portion of the translation member includes a bore for receiving the sphere to provide the polyaxial movement. A surface of the bore and a surface of the sphere may further include grooves and the other of the surface of the bore and the surface of the sphere includes ridges.

Another embodiment of the device features the engagement portion of the first connector including proximal and distal arms, at least one of the proximal and distal arms resiliently flexing open to accept the first elongate spinal fixation element and flexing back to provisionally receive the first elongate spinal fixation element with the interference fit. The first connector member may also include a slit extending between the proximal portion of the first connector member to the distal portion of the first connector member, the slit allowing the resilient flexing of the at least one of the proximal and distal arms of the engagement portion of the first connector. The first locking member may additionally include a first set screw and a hole on the first connector member and operatively associated with the slit such that threading of the first set screw into the hole moves the proximal and distal arms relative to one another to secure the first elongate spinal fixation element in the engagement portion of the first connector member. Furthermore, the slit may divide the sphere into first and second portions and wherein threading of the first set screw into the hole splays the first and second portions of the sphere to lock the polyaxial movement, fixing the first connector member relative to the translation member. The translation member may additionally include first and second translation elements, the first translation element including the proximal portion of the translation member and the second translation element including the distal portion of the translation member; and wherein the first and second translation elements are moveable relatively to each other to adjust a distance between the first and second connector members. In some embodiments the first and second translation elements move relative to each other with translation movement, substantially free of rotation. The first and second translation elements may be coupled with a dove-tail connection. The first and second translation elements may further move relative to each other along an arced path.

In another embodiment in accordance with the disclosure, a device for coupling first and second elongate spinal fixation elements includes a first connector member having proximal and distal portions, the distal portion including an engagement portion configured and dimensioned to provisionally receive the first elongate spinal fixation element with an interference fit; a second connector member having proximal and distal portions, the distal portion including an engagement portion configured and dimensioned to provisionally receive the second elongate spinal fixation element with an interference fit; a translation member having first and second portions, the proximal portion of the first connector member operatively associated with the first portion of the translation member to provide polyaxial movement of the first connector member relative to the translation member, the proximal portion of the second connector member operatively associated with the second portion of the translation member to provide polyaxial movement of the second connector member relative to the translation member; a first locking member to secure the first elongate spinal fixation element in the engagement portion of the first connector member and to lock the polyaxial movement, fixing the first connector member relative to the first translation member; and a second locking member to secure the second elongate spinal fixation element in the engagement portion of the second connector member and to lock the polyaxial movement, fixing the first connector member relative to the first translation member.

In embodiments of the device including first and second connectors, the proximal portions of the first and second connector members may include a sphere and the proximal and distal portions of the translation member include a bore for receiving the sphere to provide the respective polyaxial movement. The engagement portions of the first and second connectors may further include proximal and distal arms, at least one of the proximal and distal arms resiliently flexing open to accept the respective first or second elongate spinal fixation element and flexing back to provisionally receive the respective first or second elongate spinal fixation element with the interference fit. Additionally, the first and second connector members may include a slit extending between the proximal portion of the first connector member to the distal portion of the first connector member, the slit allowing the resilient flexing of the at least one of the proximal and distal arms of the engagement portion of the first and second connectors. The first and second locking members may additionally include a set screw and a hole on the respective first or second connector member and operatively associated with the slit such that threading of the set screw into the hole moves the proximal and distal arms relative to one another to secure the respective first or second elongate spinal fixation element in the engagement portion of the respective first or second connector member.

Further provided for, in accordance with the disclosure, is a method for interconnecting first and second elongate spinal fixation elements, the method including: provisionally fitting the first elongate spinal fixation element into an engagement portion of a first connector with an interference fit, the first connector operatively associated with a translation member to provide polyaxial movement of the first connector member relative to the translation member; attaching the second elongate spinal fixation element to a second connector, the second connector coupled to the translation member; and locking a locking member provided on the first connector thereby securing the first elongate spinal fixation element in the engagement portion of the first connector member and locking the polyaxial movement in order to fix the first connector member relative to the first translation member. In some embodiments of the device, the locking member includes a first set screw and a hole on the first connector member, and the locking step of the method for interconnecting first and second elongate spinal fixation elements further includes threading the first set screw thereby simultaneously securing the first elongate spinal fixation element and locking the polyaxial movement. It is further contemplated within the disclosure that the interconnecting step of the method may be performed within a posterior spinal fusion construct.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a perspective view of the connector member of the device of FIG. 1;

FIG. 4 is a cross-sectional view of the connector member of FIG. 3;

FIG. 5 is a cross-sectional view of the translation member of the device of FIG. 1 illustrating a dove-tail connection;

FIG. 6 is a perspective view of the translation member of the device of FIG. 1;

FIG. 7A is a side view of the an open offset connector member in accordance with the disclosure;

FIG. 7B is a cross-sectional view of the open offset connector member of FIG. 7A;

FIG. 7C is an exploded view of the locking assembly of the open offset connector member of FIG. 7A;

FIG. 7D is an assembled view of the locking assembly of the open offset connector member of FIG. 7A;

FIG. 9A is a side perspective view of a side-loading tulip element in accordance with the disclosure;

FIG. 9B is a cross-sectional view of the side-loading tulip element of FIG. 9A;

FIG. 9C is an exploded view of the locking assembly of the side-loading tulip element of FIG. 9A;

FIG. 9D is an assembled view of the locking assembly of the side-loading tulip element of FIG. 9A;

FIG. 11A is a side perspective view of a headed rod member in accordance with the disclosure;

FIG. 11B is a cross-sectional view of the headed rod member of FIG. 11A;

FIG. 11C is an exploded view of the locking assembly of the headed rod member of FIG. 11A;

FIG. 11D is an assembled view of the locking assembly of the headed rod member of FIG. 11A;

FIG. 12A is a side perspective view of a one-level connector in accordance with the disclosure;

FIG. 12B is a cross-sectional view of the one level connector of FIG. 11A;

FIG. 12C is an exploded view of the locking assembly of the one level connector of FIG. 12A;

FIG. 12D is an assembled view of the locking assembly of the one level connector of FIG. 12A;

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
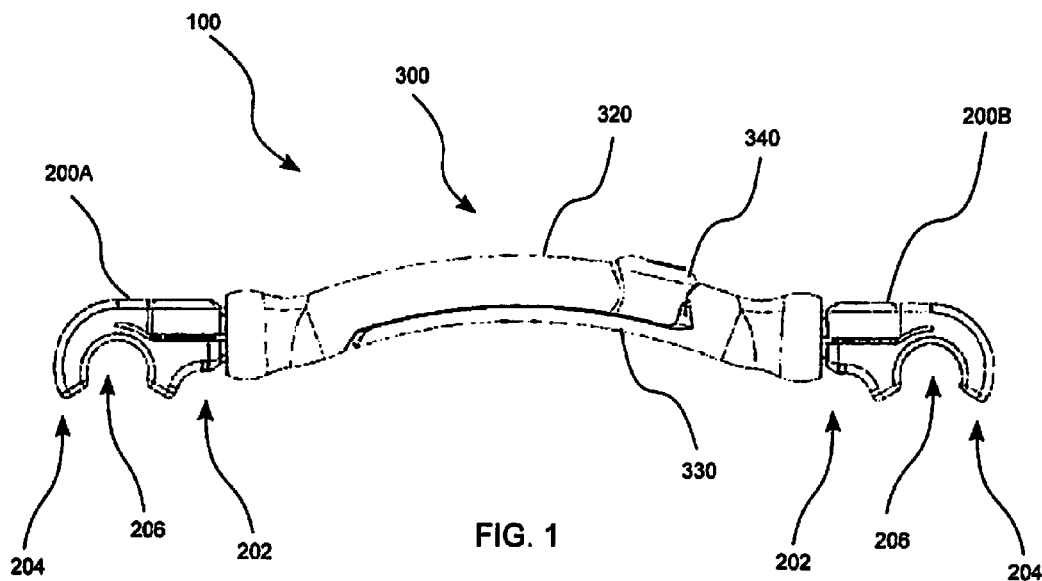
FIG. 1 is a side view of an embodiment of the cross connector device in accordance with the disclosure.

Referring now to FIG. 1, a device 100 of the disclosure is illustrated prior to receiving first and second spinal fixation elements (not illustrated). Device 100 includes first and second connector members 200A, 200B designed to receive a fixation element, and a translation member 300 cross-connecting or transconnecting first connector member 200A with second connector member 200B. In the embodiment illustrated, first connector member 200A is substantially similar to second connector member 200B, and connector members 200A, 200B are associated with opposing ends of translation member 300. Although it is advantageous to have dual connector members 200A, 200B, it should be understood that the disclosure contemplates a single connector member 200A for receiving the first fixation element while another connector, such as the alternative connectors disclosed herein or other connectors known or to be developed, connected to translation member 300 for receiving the second fixation element. Accordingly, the disclosure contemplates device 100 including any combination of connector members 200.

The spinal fixation elements to be received may include rods, plates, or other elongate members to be utilized in a spinal fixation construct, such as a posterior fusion procedure, although a variety of known or to be developed spinal fixation elements are contemplated within the disclosure. A variety of elongate member sizes are contemplated, according to the construct or situation of the surgical procedure to be performed. Examples of rod or member sizes contemplated include, but are not limited to, diameters of 4.75 mm, 5.5 mm, 6.35 mm, and other rods or members of similar sizes known or to be discovered for use in spinal fixation procedures.

Additionally referring to FIGS. 3 and 4, connector members 200A, 200B have a proximal portion 202, generally referring to the portion of connector member 200A, 200B in proximity to the translation member 300, and a distal portion 204, generally referring to the portion of the connector member 200A, 200B opposite from translation member 300. An engagement portion 206 is provided on distal portion 204 for receiving a fixation element. Proximal portion 202 is operatively associated with translation member 300 to permit polyaxial movement, including rotational movement, of connector member 200A, 200B with respect to translation member 300. Additionally provided on connector member 200A, 200B is a locking member 210, illustrated in FIGS. 3 and 4 as a set screw, operative to secure a received fixation element in engagement portion 206 while also fixing movement of connector member 200A, 200B with respect to translation member 300, i.e. locking the polyaxial movement.

Locking member 210, as illustrated in the embodiment of FIGS. 3 and 4, includes a locking screw 212 received in a threaded hole or bore 214 provided on connector member 200A, 200B. As a result of a threading or rotating, from an applied torsional force on a tool receiving upper surface of screw 212, of locking screw 212 within hole 214, screw 212 advances into hole 214 and into or towards a gap or slit 220 which extends between distal and proximal portion 202, 204. Accordingly, by displacing screw 212 into gap 220, the gap is splayed at both the distal and proximal portions 202, 204, resulting in simultaneously securing a fixation element received within engagement portion 206 as well as fixing or locking the polyaxial and rotational movement of the connector member 200A, 200B with respect to translation member 300. The splaying may be assisted by a gap wedge 222 positioned between hole 214 and gap 220 so as to exert a splaying force on gap 220 as screw 212 advances into hole 214 and presses against wedge 222.

An elongate fixation member is provisionally securable in engagement portion 206 through a snap-fit or an interference connection. Engagement portion 206 includes proximal and distal arms 208A, 208B for receiving an elongate fixation member. As an elongate fixation member is introduced into engagement portion 206, at least one of arms 208A, 208B resiliently flex open to accept the elongate fixation element and flex back to provisionally receive the fixation element with an interference fit. The interference fit may be tightened, securing the received spinal fixation element, by splaying the distal portion of gap 220. The splaying or separating of the distal portion of gap 220 widens the gap thereby moving arms 208A, 208B with respect to one another resulting in a clamping motion on a received fixation member.

Extending into a bore 310 of translation member 300 is a sphere 230 for providing polyaxial movement of connection member 200A, 200B with respect to translation member 300. The polyaxial movement is advantageous in aiding a surgeon, or other technician, installing the device to move, rotate, or adjust device 100 to connect second connector member 200B with the second elongate member while the first elongate member is provisionally received within engagement portion 206 of first connector member 200A. Once the second elongate member is connected to or secured within second connector member 200B, the polyaxial movement of first connector 200A may be fixed by locking sphere 230 within bore 310. In an embodiment of the disclosure, sphere 230 is composed of upper and lower surfaces 232, 234, separated by the proximal portion of gap 220. Locking of sphere 230 within bore 310 may accordingly occur by splaying upper and lower surfaces 232, 234 thereby forcing surfaces 232, 234 against an inner wall or surface 312 of bore 310 in order to frictionally secure sphere 230 from moving or rotating within bore 310. In some embodiments, sphere 230 will advantageously include grooves or ridges 236 provided on surfaces 232, 234 and mateable with corresponding grooves or ridges 314 provided on inner surface 312.

Splaying of both the distal and proximal portions of gap 220 advantageously result from turning or rotating locking screw 212. As screw 212 is rotated, distal and proximal portions of gap 220 are both splayed thereby securing the received elongate fixation member in engagement portion 206 as well as thereby fixing connector member 200A, 200B from polyaxial movement with respect to translation member 300. This dual locking mechanism is advantageous for quickly and efficiently securing device 100 during a surgical procedure.

Figure 2:
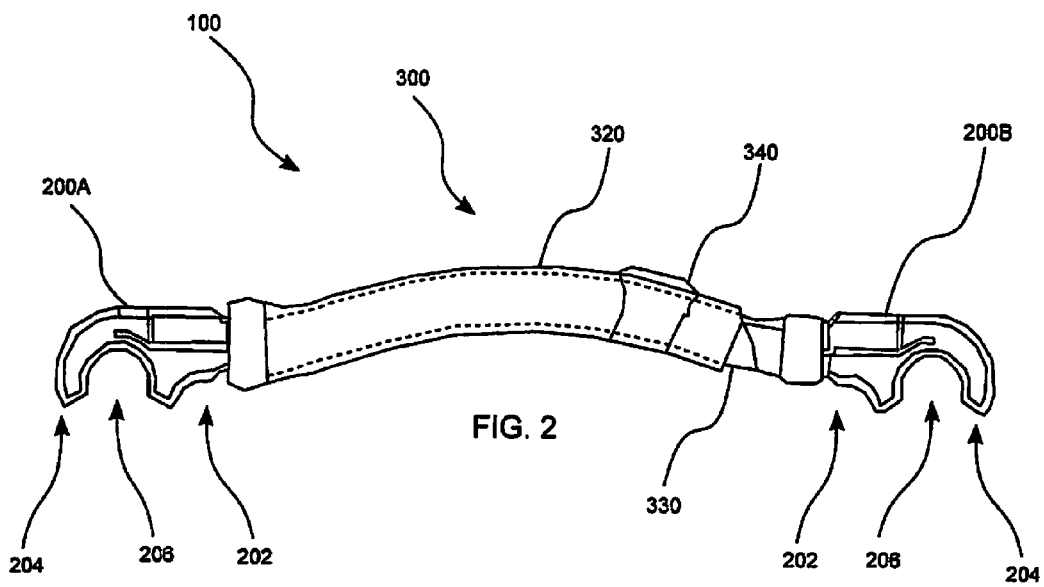
FIG. 2 is a side view of a second embodiment of a cross connector device.
Figures 8A, 8B, 8C, 8D:
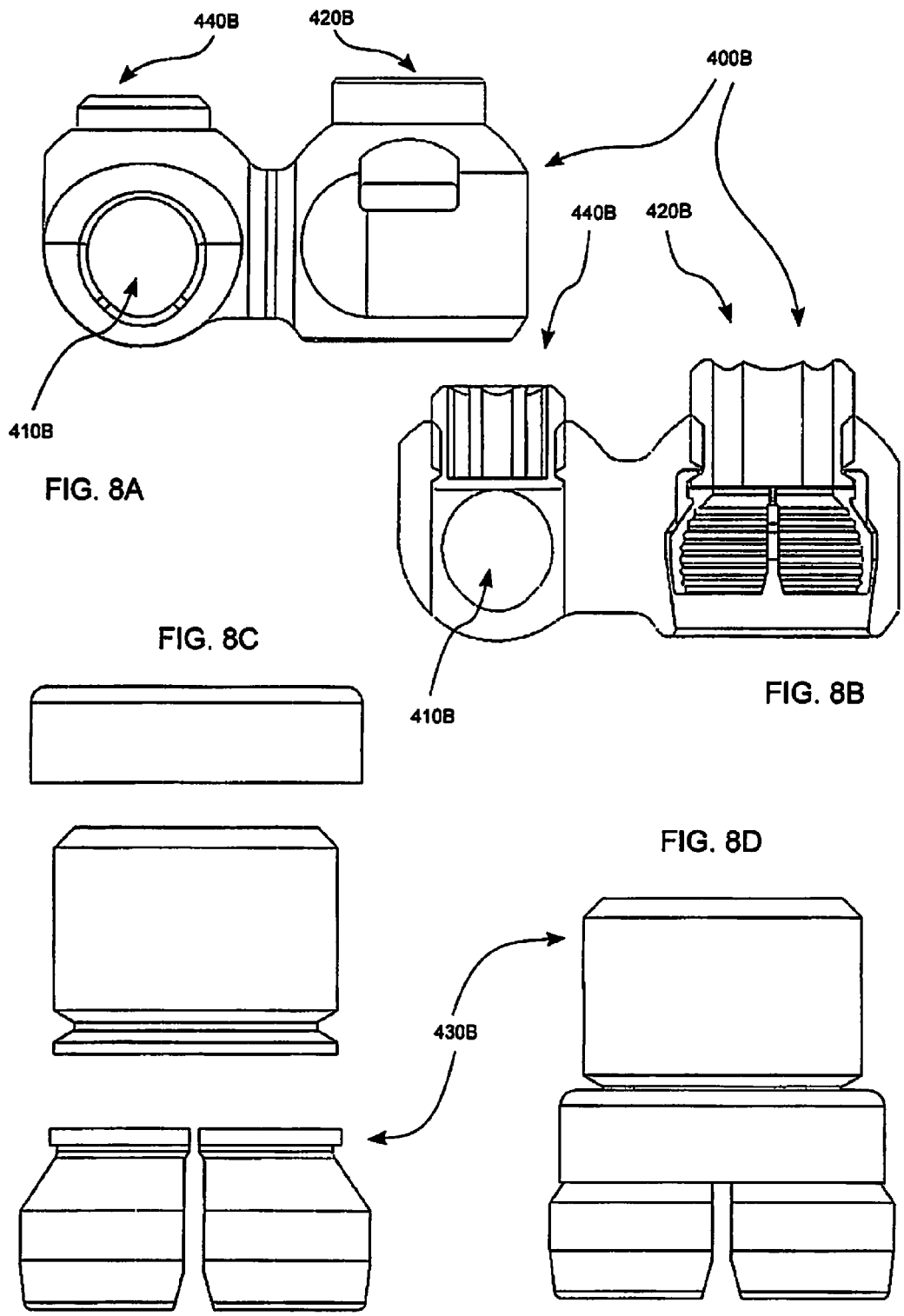
FIG. 8A is a side view of a closed offset connector member in accordance with the disclosure.
FIG. 8B is a cross-sectional view of the closed offset connector member of FIG. 8A.
FIG. 8C is an exploded view of the locking assembly of the closed offset connector member of FIG. 8A.
FIG. 8D is an assembled view of the locking assembly of the closed offset connector member of FIG. 8A.
Figure 10A:
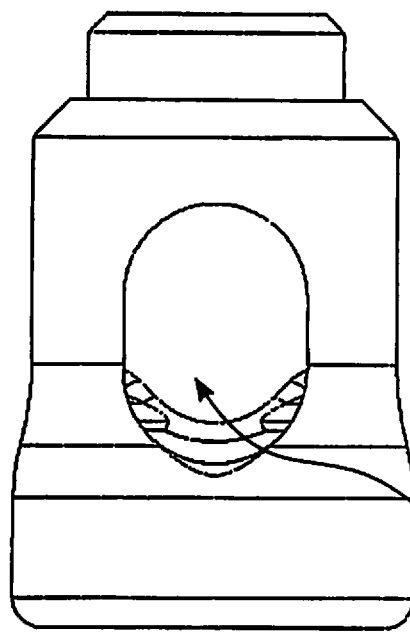
FIG. 10A is a side perspective view of a closed head tulip element in accordance with the disclosure.
Figure 10B:
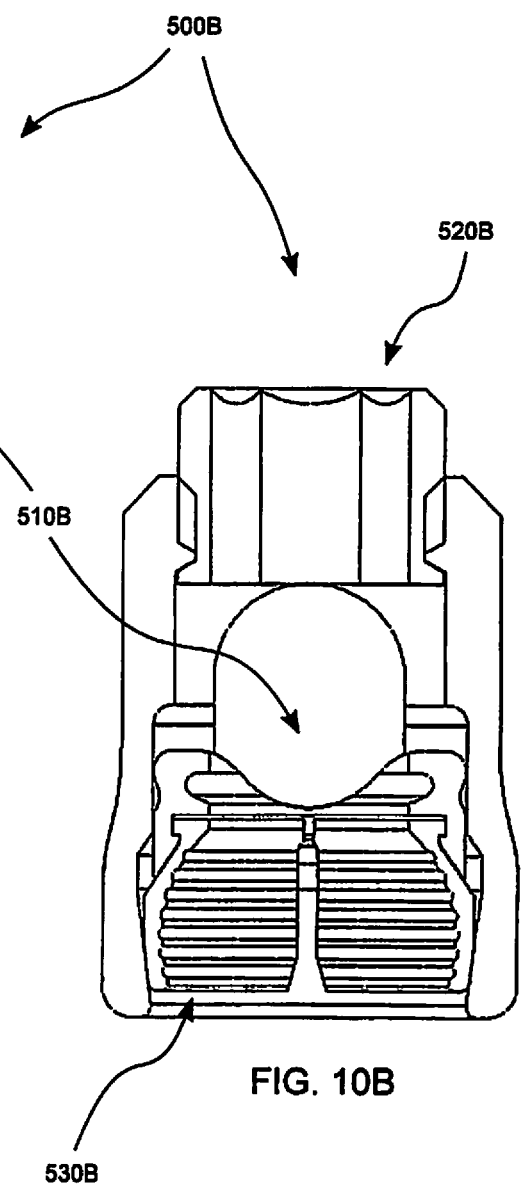
FIG. 10B is a cross-sectional view of the closed-head tulip element of FIG. 10A.

In reference now to FIGS. 5 and 6, an embodiment of translation member 300 includes first and second translation elements 320, 330. First translation element 320 is connectable with first connector member 200A and second translation element 330 is connectable with second connector member 200B. First and second translation elements 320, 330 are movable or slidable relative to one another to adjust a distance between first and second connector members 200A, 200B. This translation movement adjusting the distance between first and second connector members 200A, 200B along with polyaxial movement of connector members 200A, 200B with respect to translation member 300, provides for interconnecting first and second fixation elements. In one embodiment, first and second translation elements 320, 330 move relative to one another along an arced path. In FIG. 2, an additional embodiment is illustrated depicting second translation element 330 slidable within first translation element 320, and fixable by a third locking screw or element 340.

A locking element 340 is provided to couple first and second translation elements 320, 330 with respect to each other, thereby fixing first and second translation elements 320, 330 from moving with respect to each other and securing first and second connector elements 200A, 200B at a distance from each other. In an exemplary embodiment, locking element 340 couples first and second translation elements 320, 330 in a dovetail connection. A dovetail connection, as shown in the illustrated embodiments of FIGS. 5 and 6, provides a strong yet flexible geometry, arcing over a spinal column situated between first and second connection members 200A, 200B. With a dovetail connection, translation, with little or no rotation between translation elements 320, 330 is provided. In the embodiment illustrated in FIG. 2, first element 320 may operate to internally receive second element 330, both elements 320, 330 slidable and rotatable with respect to each other thereby establishing a distance between first and second connector members 200A, 200B.

It is contemplated within the disclosure that device 100 can be utilized as a cross-connector option for a spinal stabilization system, for example interconnecting first and second spinal fixation rods within a posterior spinal fusion construct. Device 100, in addition to the previously disclosed connector options as well as the additional connector options described herein, are components of a modular system which allows for screw tulip assembly to be attached to the screw head in-situ, following operations including, but not limited to: intervertebral operations, decortication, fusion bed preparation, etc. In reference now to FIGS. 7-13, additional embodiments of connector options which may be utilized in a spinal stabilization system will now be described.

FIGS. 7A-7D illustrate an open offset connector 400A, in accordance with the disclosure, which includes an engagement portion 410A for receiving a fixation element, a second locking set screw 420A with locking assembly 430A, and a second locking set screw 440A for securing the received fixation element. Similar to connector members 200A, 200B, the engagement portion may be advantageously received in a preliminary snap-fit or interference connection at engagement portion 410A. Second locking set screw 440A is provided to lock or clamp a received fixation element within engagement portion 410A as screw 440A is rotated or advanced into connector 400A. Open offset connector 400A may be offered in both modular and preassembled configurations allowing for an extremely low profile iliac fixation point, which is particularly advantageous for surgical procedures performed on small stature patients.

FIGS. 8A-8D illustrate a closed offset connector 400B, in accordance with the disclosure, which includes engagement portion 410B, a first locking set screw 420A with locking assembly 430, and a second locking set screw 440B for securing the received fixation element. Unlike engagement portion 410A, engagement portion 410B is closed to fully enclose a received spinal fixation element. In the embodiment disclosed, second locking set screw 420B is similar to second locking set screw 420A, and locking assembly 430B is similar to locking assembly 430A, however it should be appreciated that different locking assemblies and/or set screws for establishing bone fixation, such as iliac fixation points, may be utilized in accordance with the disclosure. Closed offset connector 400B may also be offered in both modular and preassembled configurations allowing for extremely low profile fixation points.

Referring now to FIGS. 9A-9D and FIGS. 10A-10D illustrating embodiments of tulip elements 500A, 500B which may be utilized as part of a stabilization system, in accordance with the disclosure. Side-loading tulip element 500A, includes a tulip 510A, locking set screw 520A, and a locking assembly 530A. Closed head tulip element 500B includes a tulip 510B, locking set screw 520B, and a locking assembly 530B associated with locking screw 520B. Tulip elements 500A, 500B may be offered in both modular and preassembled configuration and allow for a secure low profile fixation rod and bone screw or fastener connection point, which is particularly useful for iliac fixation in a spinal fixation procedure.

FIGS. 11A-11D illustrate a headed rod or implant 600 which may be utilized as part of a stabilization system, in accordance with the disclosure. Implant 600 includes a connector element or rod 610, locking set screw 620, and a locking assembly 630 associated with locking set screw 620. Headed rod 600 may be offered in both modular and preassembled configurations and allows for extremely low profile fixation points, for example in sacral fixation points, which is useful for small stature patients.

FIGS. 12A-12D illustrate a one level connector 700 which may be utilized as part of a stabilization system, in accordance with the disclosure. One-level connector includes first and second locking set screws 710A, 710B and first and second locking assemblies 720A, 720B associated with locking set screws 710A, 710B. One level connector 700 may be offered in both modular and preassembled configurations and allows for extremely low profile fixation points, for example in sacral fixation points, which is useful for small stature patients.

Figure 13A:
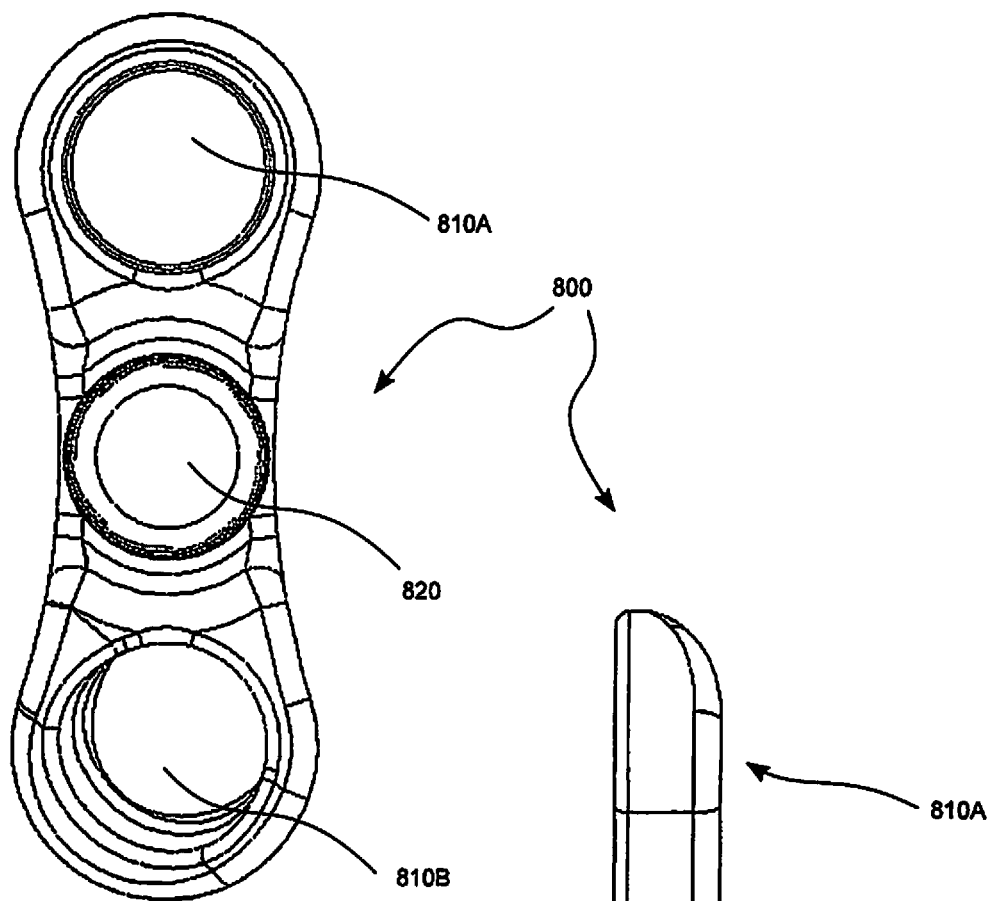
FIG. 13A is a top view of a fixation plate in accordance with the disclosure.
Figure 13B:
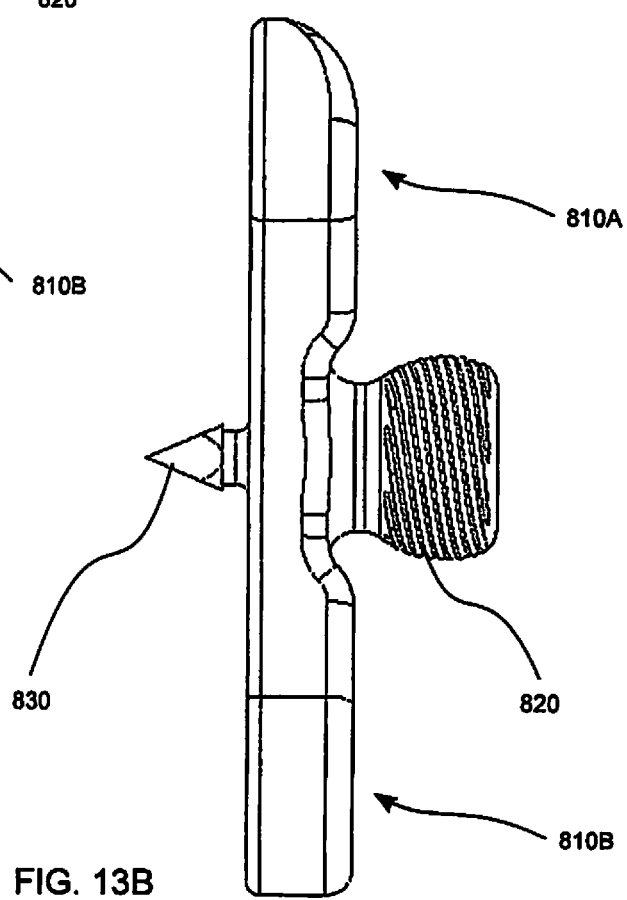
FIG. 13B is a side view of the fixation plate of FIG. 13A

FIGS. 13A and 13B illustrate a fixation plate or implant 800 which may be utilized as part of a stabilization system, including for example sacral fixation, in accordance with the disclosure. Fixation plate 800 advantageously accommodates dual-point fixation by receiving a first rod or fixation element in a first aperture 810A, and a second rod or fixation element in a second aperture 810B, thereby allowing in-situ attachment of any modular component as a part of a stabilization system. Provided on a first end of plate 800 is a protruding element 820, which in some embodiments is threaded on an exterior surface in order to mate with another element and/or to improve the grip of a technician attaching the plate as a component of a stabilization system. Provided on a surface of the plate opposite protruding element or knob 820 is a pointed element or spike 830. The one-piece design, as shown in the illustrated embodiment of plate 800, is beneficial for both manufacturing and ease of attachment as a component of a stabilization system. The dual-point fixation provided by plate 800 has shown to at least 25% stronger than traditional constructs used in similar sacral fixation elements.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A coupling device comprising:
   a connector member including an engagement portion configured and dimensioned to receive an elongate spinal fixation element;
   a translation member having an end operatively associated with the connector member to provide polyaxial movement of the connector member relative to the translation member, wherein a portion of the connector member extends through a bore formed in the translation member; and
   a locking member to secure the elongate spinal fixation element in the engagement portion of the connector member and to lock the polyaxial movement, thereby fixing the connector member relative to the translation member, wherein the locking member is received through the connector member and not the translation member.

2. The device of claim 1, wherein the portion of the connector member that extends into the translation member includes a sphere and the bore in the translation member receives the sphere to provide the polyaxial movement.

3. The device of claim 2, wherein one of a surface of the bore and a surface of the sphere includes grooves and the other of the surface of the bore and the surface of the sphere includes ridges.

4. The device of claim 2, wherein the engagement portion of the connector member includes proximal and distal arms, at least one of the proximal and distal arms resiliently flexing open to accept the elongate spinal fixation element and flexing back to provisionally receive the elongate spinal fixation element with an interference fit.

5. The device of claim 4, wherein the connector member includes a slit extending from a proximal portion of the connector member to a distal portion of the connector member, the slit allowing the resilient flexing of the at least one of the proximal and distal arms of the engagement portion of the connector.

6. The device of claim 5, wherein the locking member includes a set screw and a hole on the connector member and operatively associated with the slit such that threading of the set screw into the hole moves the proximal and distal arms relative to one another to secure the elongate spinal fixation element in the engagement portion of the connector member.

7. The device of claim 6, wherein the slit divides the sphere into first and second portions and wherein threading of the set screw into the hole splays the first and second portions of the sphere to lock the polyaxial movement, thereby fixing the connector member relative to the translation member.

8. The device of claim 7, wherein the translation member includes first and second translation elements, the first translation element including a proximal portion of the translation member and the second translation element including a distal portion of the translation member; and wherein the first and second translation elements are moveable relatively to each other.

9. The device of claim 8, wherein the first and second translation elements move relative to each other with translation movement, substantially free of rotation.

10. The device of claim 9, wherein the first and second translation elements are coupled with a dove-tail connection.

11. The device of claim 10, wherein the first and second translation elements move relative to each other along an arced path.

12. The device of claim 1, wherein the elongate spinal fixation element is a rod.

13. A coupling device comprising:
    a connector member including an engagement portion configured and dimensioned to receive an elongate spinal fixation element;
    a translation member including first and second translation elements moveable relative to one another to adjust a distance therebetween, wherein the translation member has an end operatively associated with the connector member to provide polyaxial movement of the connector member relative to the translation member, and wherein a portion of the connector member extends through a bore formed in the translation member; and
    a locking member to secure the elongate spinal fixation element in the engagement portion of the connector member and to lock the polyaxial movement, thereby fixing the connector member relative to the translation member, wherein the locking member is received through the connector member and not the translation member.

14. The device of claim 13, wherein the connector member includes a sphere and the bore in the translation member is configured to receive the sphere to provide the respective polyaxial movement.

15. The device of claim 13, wherein the engagement portion of the connector member includes proximal and distal arms, at least one of the proximal and distal arms resiliently flexing open to accept the elongate spinal fixation element and flexing back to provisionally receive the elongate spinal fixation element with an interference fit.

16. The device of claim 15, wherein the connector member includes a slit extending between a proximal portion of the connector member to a distal portion of the connector member, the slit allowing the resilient flexing of the at least one of the proximal and distal arms of the engagement portion of the connector member.

17. The device of claim 16, wherein the locking member includes a set screw and a hole on the connector member and operatively associated with the slit such that threading of the set screw into the hole moves the proximal and distal arms relative to one another to secure the elongate spinal fixation element in the engagement portion of the connector member.

18. A method for affixing a coupling device, the method comprising:
    attaching a coupling device to an elongate spinal fixation element, the coupling device comprising:
    a connector member including an engagement portion configured and dimensioned to provisionally receive the elongate spinal fixation element with an interference fit;
    a translation member having an end operatively associated with the connector member to provide polyaxial movement of the connector member relative to the translation member, wherein a portion of the connector member extends through a bore formed in the translation member; and a locking member, wherein the locking member is received through the connector member and not the translation member; and locking the locking member provided on the connector member thereby securing the spinal fixation element in the engagement portion of the connector member and locking the polyaxial movement in order to fix the connector member relative to the translation member.

19. The method of claim 18, wherein the locking member includes a set screw and a hole on the connector member, the locking step further comprising threading the set screw thereby simultaneously securing the elongate spinal fixation element and locking the polyaxial movement.

20. The method of claim 18, wherein the coupling device is attached to a posterior spinal fusion construct.

* * * * *